US012697161B2

(12) United States Patent
Gilbert

(10) Patent No.: US 12,697,161 B2
(45) Date of Patent: Aug. 4, 2026

(54) SYSTEMS, METHODS AND APPARATUSES FOR AN ELECTROSURGICAL RF GENERATOR FOR ELECTROSURGICAL CUTTING

(71) Applicant: Eximis Surgical Inc., Louisville, CO (US)

(72) Inventor: James A. Gilbert, Boulder, CO (US)

(73) Assignee: Eximis Surgical Inc., Louisville, CO (US)

( * ) Notice: Subject to any disclaimer, the term of this patent is extended or adjusted under 35 U.S.C. 154(b) by 613 days.

(21) Appl. No.: 18/195,830

(22) Filed: May 10, 2023

(65) Prior Publication Data

US 2023/0363813 A1 Nov. 16, 2023

Related U.S. Application Data

(60) Provisional application No. 63/340,397, filed on May 10, 2022, provisional application No. 63/415,377, filed on Oct. 12, 2022.

(51) Int. Cl.
*A61B 18/12* (2006.01)
*A61B 17/00* (2006.01)

(52) U.S. Cl.
CPC ..................... *A61B 18/1206* (2013.01); *A61B 2017/00526* (2013.01); *A61B 18/1233* (2013.01); *A61B 2018/1286* (2013.01)

(58) Field of Classification Search
CPC ......................... A61B 18/1206; A61B 18/1233
See application file for complete search history.

(56) References Cited

U.S. PATENT DOCUMENTS

| | | | |
|---|---|---|---|
| 4,727,874 A | 3/1988 | Bowers et al. | |
| 9,522,034 B2 | 12/2016 | Johnson et al. | |
| 9,649,147 B2 | 5/2017 | Gilbert et al. | |
| 2003/0181898 A1 | 9/2003 | Bowers | |

(Continued)

FOREIGN PATENT DOCUMENTS

WO 2023220186 A1 11/2023

OTHER PUBLICATIONS

Guo, et al., "Active Frequency Selective Surface With Wide Reconfigurable Passband", Mar. 19, 2019, pp. 38348-38355, vol. 7, Publisher: IEEE Access.

(Continued)

*Primary Examiner* — Sean W Collins
(74) *Attorney, Agent, or Firm* — Rogue.law; Laura Schneider

(57) ABSTRACT

A radiofrequency (RF) generator for use with an electrosurgical system includes a shifted, transformed LCLC bandpass filter, configured for allowing the RF generator to operate using a single electrosurgical power setting while preventing overheating of the electrosurgical system. The LCLC bandpass filter may be configured to operate with a specified power curve such that an operating current generated by the RF generator is folded back when approaching short circuit conditions. The RF generator may include a fixed, medical power supply, wherein the specified power curve is modified by switching frequency modulation of the LCLC bandpass filter. Further a method for designing a RF generator for electrosurgical application is disclosed.

9 Claims, 11 Drawing Sheets

700

Shifted, LP to BP Transform: C1' = Kx/L1'*w0^2, L2'=1/Kx*C2'*w0^2

Butterworth n=2 Normalized LC Element Values
(assuming minimum Q>2 components)

| RL/RS | L1a | C1a | C2a | L2a |
|---|---|---|---|---|
| INF | 1.4142 | 0.7071 | 0.7071 | 1.4142 |
| 10 | 0.0743 | 13.4590 | 14.8138 | 0.0675 |

Chebyshev 1-dB Ripple n=2 Normalized LC ELement Values
(assuming minimum Q>2 components)

| RL/RS | L1a | C1a | C2a | L2a |
|---|---|---|---|---|
| INF | 1.2128 | 0.8245 | 1.1093 | 0.9015 |
| 8 | 0.1571 | 6.3654 | 9.6528 | 0.1036 |

(56)                  References Cited

U.S. PATENT DOCUMENTS

| 2014/0276754 A1* | 9/2014 | Gilbert | A61B 18/1206 606/33 |
|---|---|---|---|
| 2015/0032096 A1* | 1/2015 | Johnson | A61B 18/1206 606/34 |
| 2015/0105766 A1 | 4/2015 | Johnson et al. | |
| 2017/0056092 A1* | 3/2017 | Mattmiller | A61B 18/1206 |
| 2018/0125564 A1 | 5/2018 | Johnson | |
| 2018/0256242 A1 | 9/2018 | Bluvshtein | |
| 2019/0133672 A1 | 5/2019 | Daw et al. | |
| 2021/0379393 A1* | 12/2021 | Butler | A61N 1/3981 |

OTHER PUBLICATIONS

Rodriquez, Kari, "Invitation to Pay Additional Fees and, Where Applicable, Protest Fee Re Application No. PCT/US2023/021745", Jul. 19, 2023, p. 11, Published in: WO.

Ang, "Modelling, Analysis and Design of LCLC Resonant Power Converters," University of Sheffield, Apr. 2005.

Chen, et al., "LCLC resonant converter for hold up mode operation," IEEE Conference Paper, Sep. 2015; Published in US.

WIPO, "International Search Report and Written Opinion," mailed Sep. 19, 2023, published Nov. 16, 2023 in US.

Mendelevitch, L; "Extended European Search Report and Written Opinion" for EP Application No. EP23804215; Mar. 9, 2026; 8 pages; European Patent Office; Munich, Germany.

Jensen, Scott et al.; "Modeling and Digital Control of LCLC Resonant Inverter with Varying Load"; Sep. 17, 2011; 7 pages; Energy Conversion Congress and Exposition (ECCE), 2011 IEEE, IEEE, pp. 3823-3829, XP032067680, DOI: 10.1109/ECCE.2011.6064288; ISBN: 978-1-4577-0542-7.

\* cited by examiner

Output Voltage Magnitude

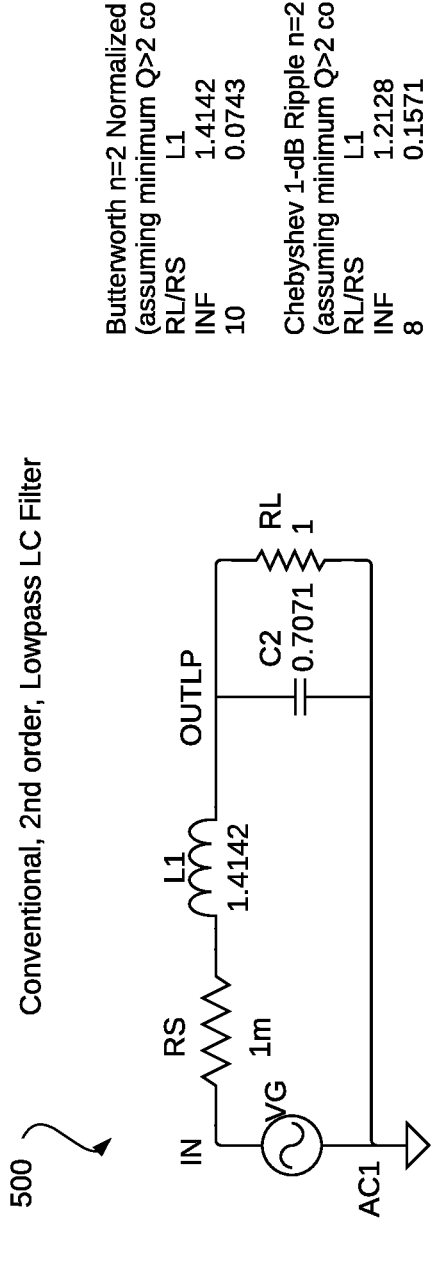

Conventional, 2nd order, Lowpass LC Filter

500

IN — RS — L1 1.4142 — OUTLP — C2 0.7071 — RL 1 — VG 1m — AC1

Conventional, LP to BP Transform: $w_0 = w_c$, $C_1 = 1/L_1 \cdot w_0^2$, $L_1/C_2 \cdot w_0^2$ IN — RS1 1m — C1a 0.7071 — L1a 1.4142 — OUTBP — L2a 1.4142 — C2a 0.7071 — RL1 1

Butterworth n=2 Normalized LC Element Values
(assuming minimum Q>2 components)

| RL/RS | L1 | C2 |
|---|---|---|
| INF | 1.4142 | 0.7071 |
| 10 | 0.0743 | 14.8138 |

Chebyshev 1-dB Ripple n=2 Normalized LC Element Values
(assuming minimum Q>2 components)

| RL/RS | L1 | C2 |
|---|---|---|
| INF | 1.2128 | 1.1093 |
| 8 | 0.1571 | 6.6582 |

Butterworth n=2 Normalized LC Element Values
(assuming minimum Q>2 components)

| RL/RS | L1a | C1a | L2a | C2a |
|---|---|---|---|---|
| INF | 1.4142 | 0.7071 | 1.4142 | 0.7071 |
| 10 | 0.0743 | 13.4590 | 0.0675 | 14.8138 |

Chebyshev 1-dB Ripple n=2 Normalized LC ELement Values
(assuming minimum Q>2 components)

| RL/RS | L1a | C1a | L2a | C2a |
|---|---|---|---|---|
| INF | 1.2128 | 0.8245 | 0.9015 | 1.1093 |
| 8 | 0.1571 | 6.3654 | 0.1036 | 9.6528 |

FIG. 5

Shifted, LP to BP Transform: C1' = Kx/L1'*w0^2, L2'=1/Kx*C2'*w0^2
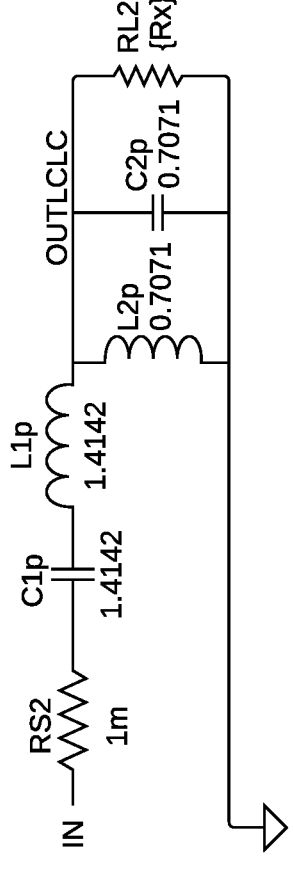
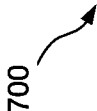
700
Butterworth n=2 Normalized LC Element Values
(assuming minimum Q>2 components)
| RL/RS | L1a | C1a | C2a | L2a |
|---|---|---|---|---|
| INF | 1.4142 | 0.7071 | 0.7071 | 1.4142 |
| 10 | 0.0743 | 13.4590 | 14.8138 | 0.0675 |
Chebyshev 1-dB Ripple n=2 Normalized LC ELement Values
(assuming minimum Q>2 components)
| RL/RS | L1a | C1a | C2a | L2a |
|---|---|---|---|---|
| INF | 1.2128 | 0.8245 | 1.1093 | 0.9015 |
| 8 | 0.1571 | 6.3654 | 9.6528 | 0.1036 |
FIG. 7

SYSTEMS, METHODS AND APPARATUSES FOR AN ELECTROSURGICAL RF GENERATOR FOR ELECTROSURGICAL CUTTING

REFERENCE TO RELATED APPLICATIONS

The present application claims the benefit of U.S. Provisional Pat. App. No. 63/340,397, filed 2022 May 10 and titled "Systems, Methods and Apparatuses for an Electrosurgical RF Generator for Electrosurgical Cutting," and U.S. Provisional Pat. App. No. 63/415,377, filed 2022 Oct. 12 and titled "Systems, Methods and Apparatuses for an Electrosurgical RF Generator for Electrosurgical Cutting."

Further, the present application relates to U.S. patent application Ser. No. 14/805,358, filed 2016 Dec. 20 and titled "Large Volume Tissue Reduction and Removal System and Method," now U.S. Pat. No. 9,522,034, and U.S. patent application Ser. No. 15/266,903, filed 2017 May 16 and titled "Electrosurgical device and methods," now U.S. Pat. No. 9,649,147.

All of the above referenced applications are incorporated hereby in their entirety by reference.

FIELD OF THE INVENTION

The present disclosure relates generally to surgical devices. In particular, but not by way of limitation, the present disclosure relates to systems, methods, and apparatuses for an electrosurgical radiofrequency (RF) generator for electrosurgical cutting.

DESCRIPTION OF RELATED ART

Tissue specimen removal systems are advanced electrosurgical systems that capture tissue by using electrosurgical cutting (see, for example, above-referenced U.S. Pat. Nos. 9,522,034 and 9,649,147). Removing tissue specimens safely, quickly, precisely, and without overheating requires great skill and care. Improvements in each of these aspects are continuously sought. In particular, there is a need for an efficient and effective electrosurgical RF generator that is operable without overheating.

SUMMARY OF THE INVENTION

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Embodiments disclosed herein address the above stated need by presenting systems, methods and apparatuses for an RF generator for use with electrosurgical systems, such as for electrosurgical cutting of various tissue specimens in various tissue specimen removal systems. In certain embodiments, the RF generator includes an LCLC (i.e., an electronic circuitry unit including a combination of two inductors and two capacitors) resonant RF inverter for the electrosurgical cutting of various tissue specimens in various tissue specimen removal systems that is capable of operating using only a single electrosurgical power setting, and preventing potentially damaging overheating of the tissue specimen removal system and secured removal of tissue specimens from a patient. It is noted that the terms "resonant inverter," "resonant RF inverter, "bandpass filter," and "resonant network" may be used interchangeably throughout the present disclosure.

In an embodiment, an electrosurgical RF generator is configured to be operated using only a single electrosurgical power setting in operating a tissue specimen removal system. In certain embodiments, the electrosurgical RF generator is configured to operate with a specified power curve wherein an operating current is folded back when approaching short circuit conditions, thus preventing potentially damaging overheating of the tissue specimen removal system while enabling secured removal of tissue specimen from a patient. That is, full output current is allowed during normal operation of the electrosurgical RF generator, while the operating current is reduced (i.e., folded back) when approaching short circuit to limit power dissipation and thermal runaway so the circuitry remains within the safe operating area of the electrosurgical RF generator.

In another embodiment, a method of operating an electrosurgical RF generator for use with a tissue specimen removal system includes: 1) identifying one or more power curve envelope candidates; 2) specifying an initial real power versus tissue resistance envelope; 3) using ideal open loop output characteristics of an inverter to determine a characteristic output impedance of the electrosurgical RF generator to be designed; 4) identifying a current and voltage limiting region; 5) determining a tolerance in the voltage and current limits in consideration of a region of uncertainty in power on the power curve; 6) calculating a first iteration of an output network characteristic impedance to be used for initial tissue testing.

In an embodiment, the electrosurgical RF generator includes an LCLC resonant network configured for implementing a pulse width modulation (PWM) scheme. The electrosurgical RF generator may further include first stage power factor correction (PFC) alternating current (AC)—direct current (DC) conversion, followed by a secondary DC-DC buck or boost stage for adjusting an input voltage to the LCLC resonant network. In certain aspects, the electrosurgical RF generator so designed avoids energy overdosage and maintains a monotonic power setting by modifying the power curve. In embodiments, the electrosurgical RF generator includes a fixed, medical power supply, and the power curve is modified by switching frequency modulation of the LCLC resonant network. In certain embodiments, the electrosurgical RF generator includes a bandpass network configured for simultaneously exhibiting the following characteristics: a) substantially maintains zero-voltage switching (ZVS) over a load range from short circuit to open circuit; b) meets a selected, near-ideal, characteristic output impedance over the load range; and c) limits the harmonic frequency content over the load range to levels safely within International Electrotechnical Commission (IEC) limits.

In a further aspect, the method of operating the electrosurgical RF generator further includes: 7) determining a harmonic content of the output waveform; 8) providing a normalized LCLC bandpass filter; and 9) transforming the normalized filter to a desired center frequency $f_c$ and load impedance $R_L$ by modification of scaling factors $K_f$ and $K_m$, respectively, specified in one or more equations defining filter components.

In embodiments, the electrosurgical RF generator may further include additional components such as a display and nonvolatile memory coupled to a bus that is also coupled to random access memory ("RAM"), a processing portion (which may include a plurality of processing components), a field programmable gate array (FPGA), and a transceiver component (which may include a plurality of transceivers).

These and other features, and characteristics of embodiments of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF DRAWINGS

FIG. 5 illustrates a design procedure for a normalized LCLC bandpass filter using a low-pass (LP) to bandpass (BP) transformation technique according to Butterworth and Chebyshev 1-dB ripple filter alignments, in accordance with embodiments.

FIG. 7 illustrates a shifting procedure for further scaling the LCLC network characteristics, in accordance with embodiments.

Figure 1:
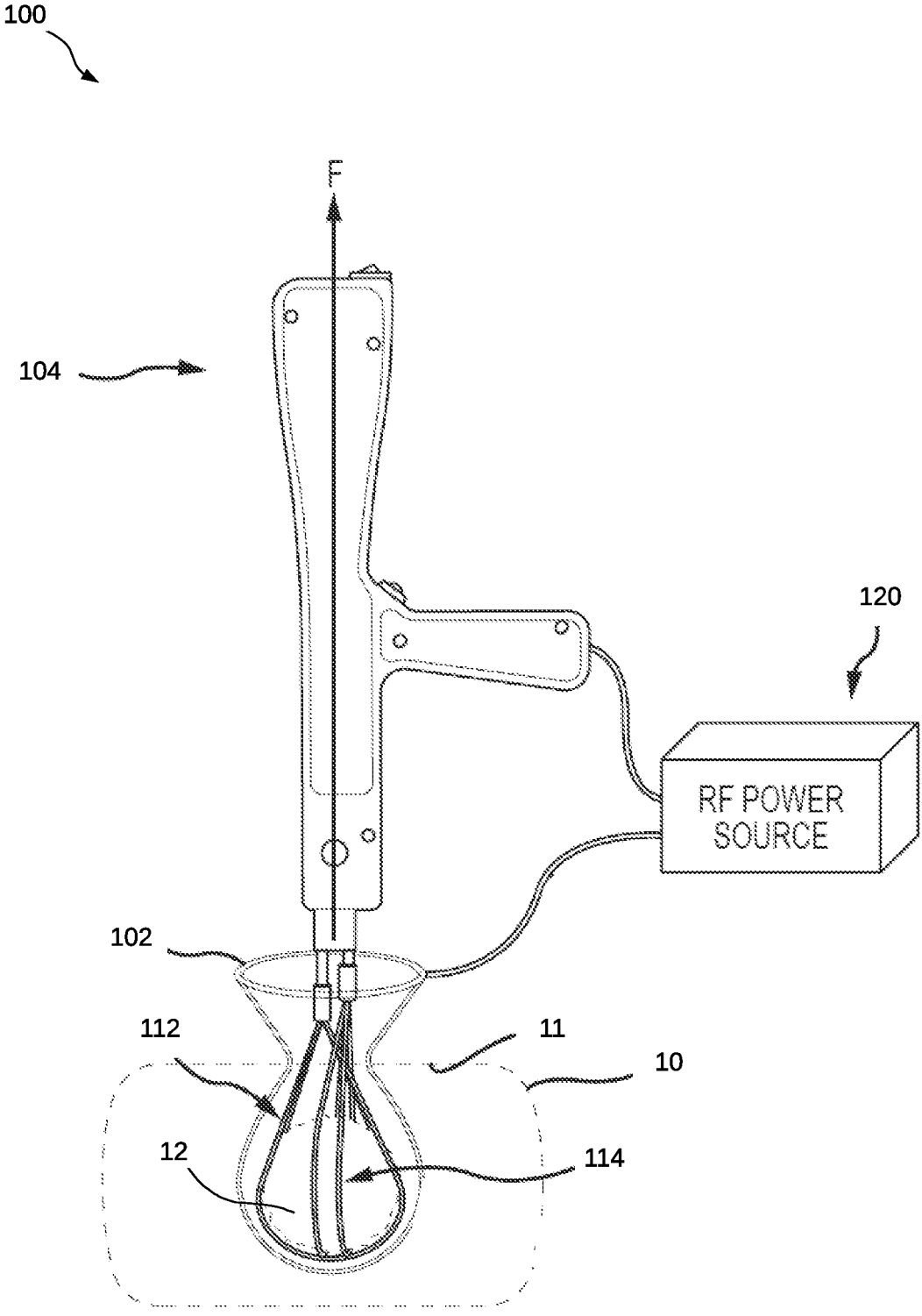
FIG. 1 illustrates an example of an electrosurgical system operated using an RF power source.

For simplicity and clarity of illustration, the drawing figures illustrate the general manner of construction, and descriptions and details of well-known features and techniques may be omitted to avoid unnecessarily obscuring the embodiments detailed herein. Additionally, elements in the drawing figures are not necessarily drawn to scale. For example, the dimensions of some of the elements in the figures may be exaggerated relative to other elements to help improve understanding of the described embodiments. The same reference numerals in different figures denote the same elements.

The word "exemplary" is used herein to mean "serving as an example, instance, or illustration." Any embodiment described herein as "exemplary" is not necessarily to be construed as preferred or advantageous over other embodiments. In the following detailed description, references are made to the accompanying drawings that form a part hereof, and in which are shown by way of illustrations or specific examples. These aspects may be combined, other aspects may be utilized, and structural changes may be made without departing from the present disclosure. Example aspects may be practiced as methods, systems, or apparatuses. The following detailed description is therefore not to be taken in a limiting sense, and the scope of the present disclosure is defined by the appended claims and their equivalents.

DETAILED DESCRIPTION OF THE INVENTION

The word "exemplary" is used herein to mean "serving as an example, instance, or illustration." Any embodiment described herein as "exemplary" is not necessarily to be construed as preferred or advantageous over other embodiments.

Preliminary note: the flowcharts and block diagrams in the following Figures illustrate the functionality and operation of possible implementations of an electrosurgical RF generator according to various embodiments of the present disclosure. It should be noted that, in some alternative implementations, the functions noted in each block may occur out of the order noted in the figures. For example, two blocks shown in succession may, in fact, be executed substantially concurrently, or the blocks may sometimes be executed in the reverse order, depending upon the functionality involved.

The embodiments described below are not intended to limit the disclosure to the precise form disclosed, nor are they intended to be exhaustive. Rather, the embodiment is presented to provide a description so that others skilled in the art may utilize its teachings. Technology continues to develop, and elements of the described and disclosed embodiments may be replaced by improved and enhanced items, however the teaching of the present disclosure inherently discloses elements used in embodiments incorporating technology available at the time of this disclosure.

The figures described in greater detail below illustrate a method for designing and operating an electrosurgical RF generator, such as an LCLC resonant RF inverter, for electrosurgical cutting in accordance with one or more implementations. Further, embodiments of an electrosurgical RF generator implemented in accordance with the design method are also described herein. The RF generator and operations of the method presented below are intended to be illustrative. In some implementations, the method may be accomplished with one or more additional operations not described, and/or without one or more of the operations discussed. Additionally, the order in which the operations of the method are illustrated in the figures and described below is not intended to be limiting.

FIG. 1 shows an exemplary electrosurgical system, such as described in the related patent documents referenced above, for performing operations within an internal cavity 10 of a patient (not shown). In certain examples, internal cavity 10 (such as a uterus) may be defined by an interior wall 11 (such as the uterine wall) surrounding a specimen 12 to be removed from the patient.

As shown in FIG. 1, the exemplary electrosurgical system may be a tissue removal device 100. For example, tissue removal device 100 includes a retrieval bag 102 connected with an actuator 104. Retrieval bag 102 may be inserted into internal cavity 10 via a small incision made in interior wall 11, then positioned around specimen 12. In embodiments, actuator 104 may include, for example, a first set of electrodes 112 and a second set of electrodes 114 configured for placement around specimen 12. Actuator 104 is electrically coupled with a RF power source 120, which provides power to first and second sets of electrodes to segment specimen 12 into smaller pieces within retrieval bag 102 via electrical energy and/or a proximal force F. Segmented specimen 12 may then be removed from retrieval bag then, in certain embodiments, retrieval bag 102 may also include electrically activated compression mechanisms, connected with RF power source 120, to deflate retrieval bag 102 for facilitating removal from the patient. It would be desirable to minimize any incision made through internal cavity 10 and to [0033] avoid damage to interior wall 11. A particular concern in an electrosurgical system such as tissue removal device 100 is thermal damage to interior wall 11 due to overheating of components placed within internal cavity 10.

For successful segmentation, the wire exposure area (i.e., area of the specimen in contact to the wires forming the electrodes) must maintain a minimum current and power density to sustain the cut and an adequate voltage to initiate the cut for the segmentation. For larger specimens, the wire exposure area must also increase, thus requiring the RF power source to provide a higher current and power into lower impedance ranges. Smaller specimens may require less current and power. Overheating of the electrodes and/or specimen bag may occur, for instance, if RF power source 120 does not provide power at levels and with parameters suitable for the specific specimen of interest.

Certain embodiments of a RF power source suitable for use with electrosurgical systems may be based on LCLC topology (i.e., a circuit block including a combination of two inductors and two capacitors). While LCLC output networks for inverters have been employed in applications ranging from RF induction heating to lighting ballast applications, LCLC inverters typically tend to either not see a wide range of load or may be tolerant of high harmonic content, as may be required in operating an electrosurgical system as described herein.

To address this variation in the power requirements of the electrosurgical system described above, the LCLC inverter parameters may be adjusted if the wire exposure, tissue properties or cable impedance are changed. For instance, the operational parameters of the RF power source may be unique to a particular wire exposure area, namely the length of wire and wire diameter in combination of the impedance of the cable connecting the RF power source to the actuator and/or the specimen bag, which creates the impedance load value and range observed by the inverter. In embodiments, the parameters may be adjusted to currents as low as 150 mA and as high as 5 A to accommodate a broad range of tissue specimen sizes. The required power ranges may also be adjusted to RF output as low as 15 W to as high as 600 W with the natural inverter output if the appropriate control measures are put in place to limit the power to a safe level across the entire impedance range. Further, the required open loop voltage may be adjusted to as low as 75 V and as high as 700 V as the proximity of the wire electrode and gap between the active electrode and the tissue is reduced requiring lower voltage, or the voltage required for initiation becomes larger due to the tissue properties or material properties of the electrode surface.

In certain embodiments, the RF power source may be sufficiently flexible to enable, for instance, tissue removal device 100 to provide large specimen removal, including fast, fully-contained specimen segmentation, through only a small incision. In embodiments, the RF generator may require only a single electrosurgical power setting, with a power curve where current is folded back when approaching short circuit conditions, thus preventing potentially damaging overheating of the specimen removal bag.

Figure 2:
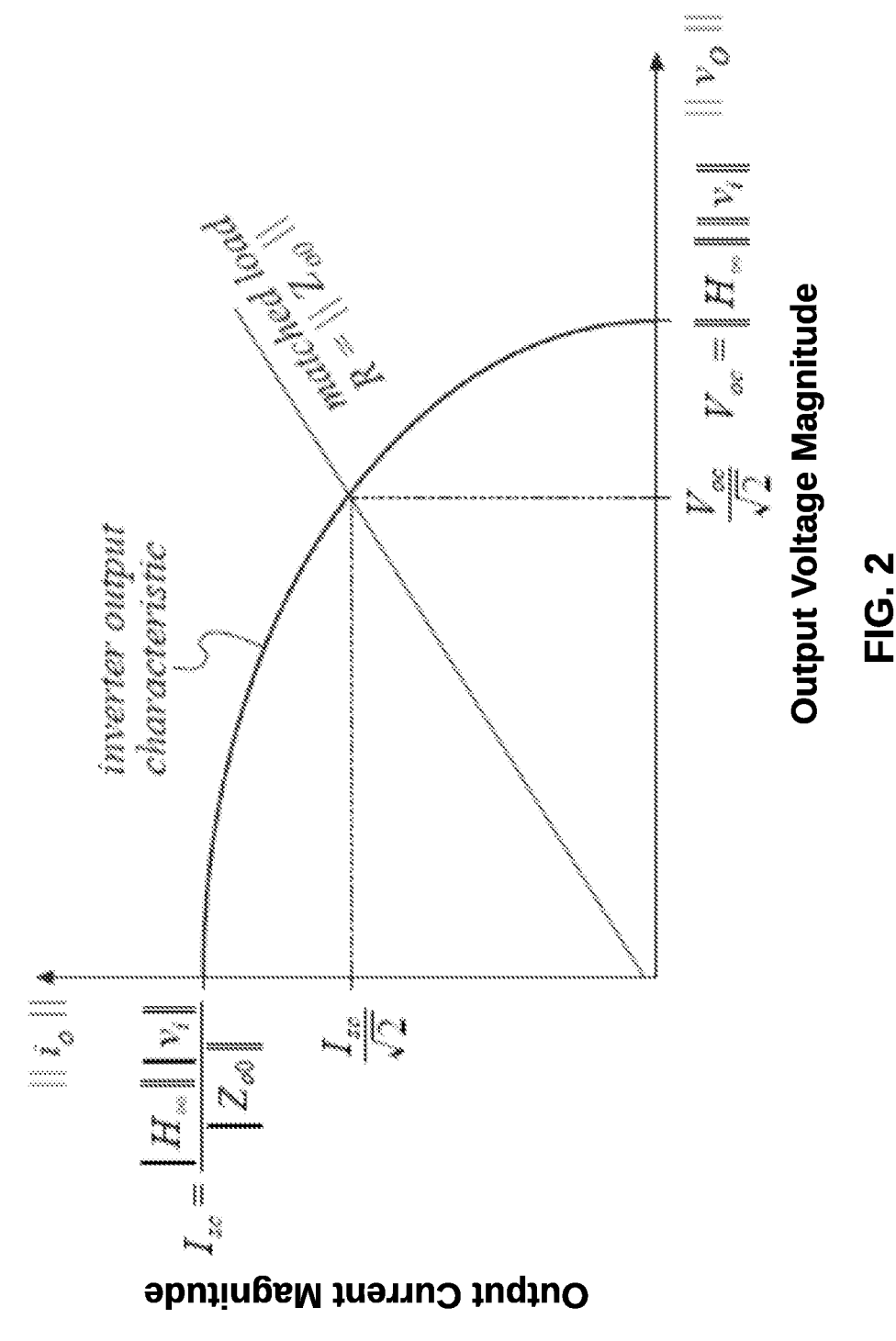
FIG. 2 illustrates open loop output characteristics of an ideal inverter.

In specifying the appropriate operational parameters for an electrosurgical RF generator as described above, we begin with an ideal open loop output characteristics of inverter. FIG. 2 shows the I-V (current as a function of voltage) curve of an ideal inverter, shown here to illustrate the elliptical output characteristics of resonant inverters. Particularly, the solid elliptical curve of plot 200 shown in FIG. 2 represents the ideal open loop output characteristics of an inverter (FIG. 19.32 from Chapter 19 of Erickson and Maksimovic, Fundamentals of Power Electronics, 2001, https://doi.org/10.1007/b100747).

In an embodiment, an initial real power versus tissue resistance envelope may be specified as beginning with a 2.5 Arms (Amps root mean square) limit up to a maximum power of 357 W (watts), which yields a resistance intersect at 60 ohms. The power curve envelope may also be specified to be substantially flat in power until a maximum voltage of 325 $V_{rms}$ (Volts root mean square) is reached, yielding a resistance intersect point of 280 ohms. Comparing to the ideal inverter characteristics shown in FIG. 2, the desired characteristics corresponding to these specified numbers approximately correspond to a characteristic output impedance of approximately 130 ohms and 406 W peak.

Figure 3:
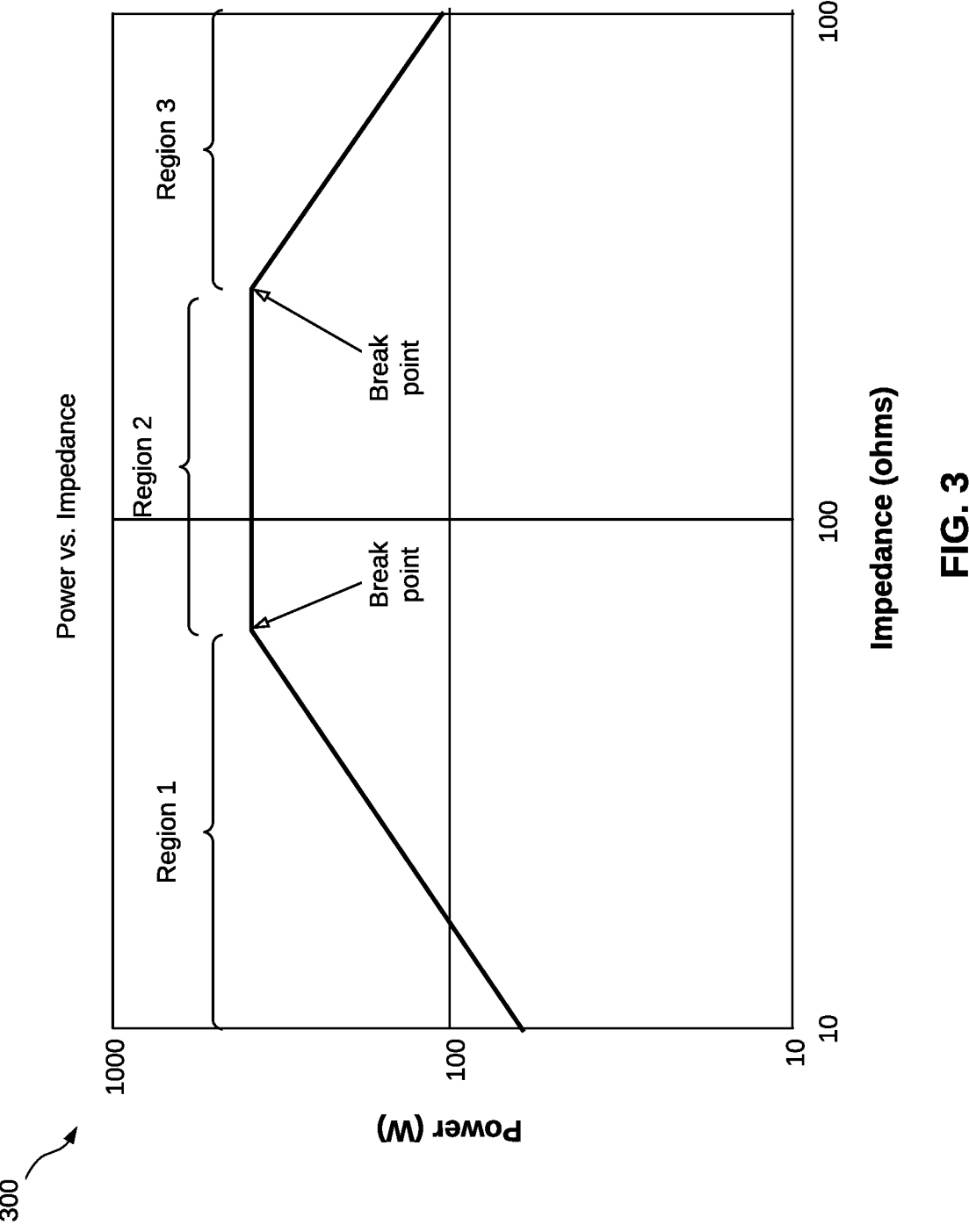
FIG. 3 shows an initially specified power curve, applying the principles of an open loop output characteristic of the ideal inverter.

An initially specified power curve 300 is shown in FIG. 3, showing a plot of power as a function of impedance using a log-log scale, in accordance with an embodiment. The log-log scale is intended to more clearly convey the current and voltage limiting regions, namely Regions 2 and 3 of FIG. 3.

It may be noted that the International Electrotechnical Commission (IEC) requires a 20% tolerance in power accuracy, in order to avoid energy overdosage while maintaining power settings that are monotonic (i.e., increases and/or decreases in intended directions), without creating unrealistic requirements for situations of energy underdosage. It is recognized herein that, the tolerance requirement of 20% in power (y-axis of FIG. 3) in Region 2 arises due to the fact that power=voltage×current and impedance=voltage/current. This 20% tolerance requirement in power setting in Region 2 implies that the tolerance on the load impedance (x-axis of FIG. 3) at the breakpoints for regions 1 and 3 is also 20%.

The power curve of FIG. 3 may be modified to limit the maximum power to less than 400 W, which is the IEC maximum power limit for electrosurgical systems, including a 20% tolerance margin. As a result, the nominal power is limited to 333 W, while retaining the same voltage and current limit requirements. This modification ensures the IEC maximum limit is not exceeded while limiting only the range over which the power must be limited by a control loop, without affecting the necessary open loop characteristics.

Limitation of the maximum power may be provided, by way of example and not limited to: 1) using a pulse width modulation (PWM) scheme with an LCLC resonant network; 2) providing a first stage power factor correction (PFC) alternating current to direct current (AC-DC) conversion followed by a secondary direct current to direct current (DC-DC) buck or boost stage to adjust the input voltage; and 3) using a combination of a fixed medical power supply (e.g., a commercial "off the shelf" power supply providing 48 $V_{DC}$) and switching frequency modulation of the LCLC resonant network. The third approach is advantageous in accommodating the use of proven, commercial power supplies in tandem with frequency modulation schemes that are found in LLC (i.e., circuitry unit combining two inductors with a capacitor) resonant converters commonly used in, for example, lighting and battery charging applications. Further, this third approach does not require the design of a second stage and multiple control loops, thus eliminating additional circuit design costs and accounting for potentially complex interactions of the control loops.

Another consideration for specifying the LCLC inverter characteristics for the electrosurgical RF generator is the harmonic content of the output waveform. It is noted that most LLC resonant designs actually yield converters, not inverters, since the switching waveforms are generally rectified then low pass filtered to yield essentially a DC voltage. For example, at light loads to open circuits, series LLC networks exhibit nearly square wave output waveforms before rectification and low pass filtering. Also, while LLC resonant converters exhibit good attenuation of high frequency content in series form, they do not provide current limiting or DC protection of the transformer under fault when in parallel form.

Figure 4:
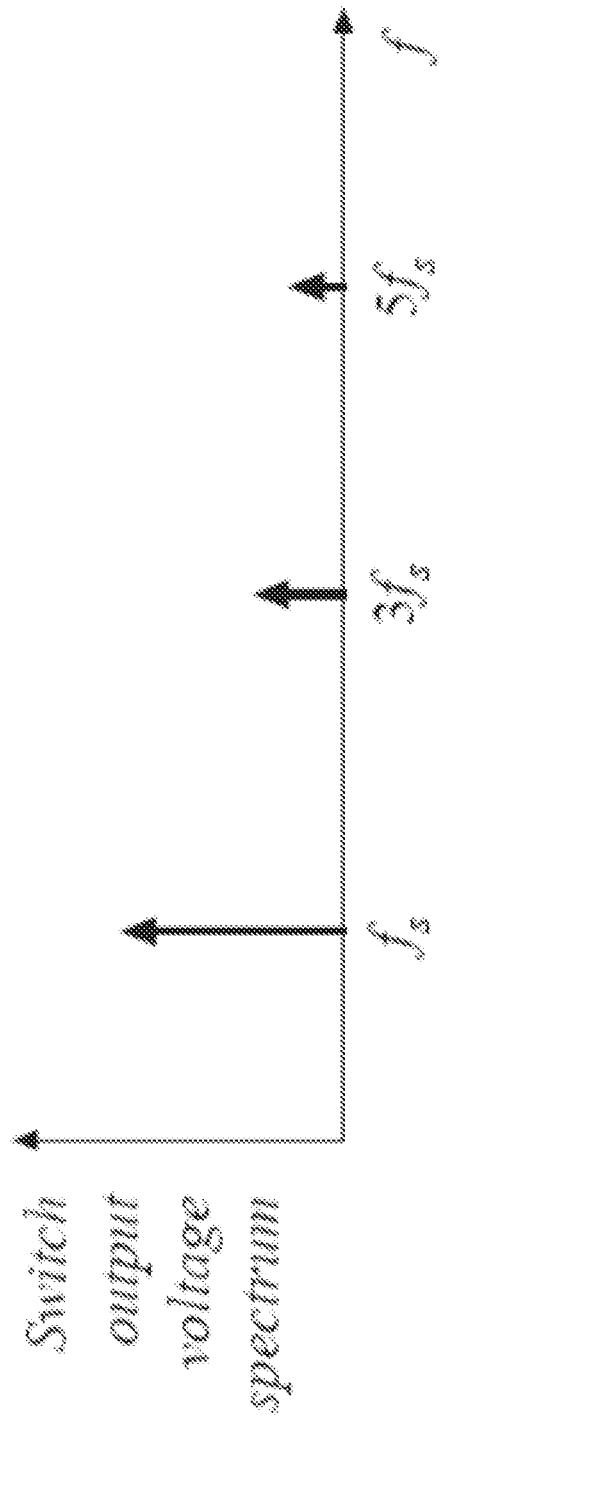
FIG. 4 shows high, primarily odd order, harmonic content, suitable for use with inverter applications such as electrosurgery, in accordance with embodiments.

An example of a high, primarily odd-order harmonic content is shown in FIG. 4 (for further details, see FIG. 19.2 and explanatory paragraphs of Erickson and Maksimovic, referenced above). When integrated into inverter applications, such as electrosurgery, the use of an input with such characteristics may lead to issues with high peak voltages at light loads as well as high frequency leakage. Such issues are particularly problematic due to the potential for capacitive coupling to alternate paths, which may result in RF burns of the patient or any medical personnel in physical contact with the patient. Therefore, it is recognized herein that it would be desirable to reduce or eliminate the high frequency content of the RF waveform provided by the RF generator in electrosurgical applications.

Further, it is recognized herein that strong odd harmonic content is a pervasive problem for series LLC networks at open circuit. Further, strong even order harmonic content may also be present in series LLC networks due to dead-time (or PWM at low power levels) during nominal loading situations. Theoretically, a LLC network topology for electrosurgical RF generators may be designed to make such harmonic content tolerable by including a modest low pass filter feature at or near the 5th harmonic and above for a 200 kHz minimum frequency system, for example, to satisfy IEC requirements. However, such modifications may affect the zero-voltage-switching (ZVS) characteristics of the LLC circuitry. Particularly given the higher coupling capacitance exhibited by some electrosurgical applications, such as the tissue removal system described above, such design-around approaches are not always effective. Therefore, rather than a power limiting approaches based on a series LLC network and PWM control, the disclosure below focuses on the implementation of a LCLC network capable of achieving a bandpass limiting function over the desired range of load impedance values.

In particular, it would be desirable to achieve a LCLC output network for inverters capable of accommodating a very wide range of load at the output and/or tolerant of high harmonic content at the input. Further, it would be desirable to achieve a bandpass network simultaneously capable of maintaining ZVS of a wide range of load (e.g., from short circuit to open circuit), meets a selected, near-ideal characteristic output impedance over the load range, and limits the harmonic frequency content over the load range to levels that would be safely within IEC limits.

In previously available LCLC bandpass filter (BPF) designs for RF networks, such designs are generally intended for near lossless, narrowband filtering with a power factor of zero, when driven at a center resonant frequency. While the "lossless" aspect would be advantageous in the present context of electrosurgical RF generators, a power factor of zero is undesirable as this characteristic does not enable maintaining ZVS over the load impedance range. Further, in the present context, it would be desirable to meet the ZVS maintenance requirement at the primary harmonics, such that the input resistance of the filter network at each significant harmonic appears inductive (e.g., ideally exhibit a 90-degree positive phase lag) to force commutation and avoid the Miller plateau region.

FIG. 5 shows an exemplary design parameters for a normalized LCLC bandpass filter using a lowpass (LP) to bandpass (BP) transformation technique for Butterworth and Chebyshev 1-dB ripple filter alignments using a LC filter design tool (LTSpice® electronic circuit simulator in this case). Other alignments, such as Bessel or elliptic, may be considered. It is recognized herein that the Butterworth alignment generally yields an LCLC bandpass filter with a well-behaved time response with minimal overshoot. Conversely, the Chebyshev 1-dB ripple filter alignment tends to yield relatively high stop band attenuation in a narrow band.

As shown in the upper half of FIG. 5, the process begins with defining a conventional, second order low pass LC filter, assuming minimum Q>2 components for both Butterworth and Chebyshev 1-dB ripple approaches. Then, as shown in the bottom half of FIG. 5, an LP to BP transformation is performed using the following transformation relationships:

$$\omega_0 = \omega_C \text{(frequency of center passband)} \qquad \text{[Eq. 1]}$$

$$C1 = 1/(L1 * \omega_0\hat{~}2) \qquad \text{[Eq. 2]}$$

$$L2 = 1/(C2 * \omega_0\hat{~}2) \qquad \text{[Eq. 3]}$$

Using the relationships in Eqs. 1-3, the LC filter parameters calculated in the top half of FIG. 5 may be converted to a normalized bandpass LCLC bandpass filter. Then, the results are further transformed to a desired center frequency $f_C$ and load impedance $R_L$ using scaling factors $K_f$ and $K_m$ of the filter components as given by the following:

$$K_f = 2\pi f_c \qquad \text{[Eq. 4]}$$

$$K_m = R_L \qquad \text{[Eq. 5]}$$

$$L' = L/K_f \qquad \text{[Eq. 6]}$$

$$C' = C/K_f \qquad \text{[Eq. 7]}$$

$$R' = RK_m \qquad \text{[Eq. 8]}$$

$$L' = LK_m \qquad \text{[Eq. 9]}$$

$$C' = C/K_m \qquad \text{[Eq. 10]}$$

The impedance magnitude scaling factor across the output transformer is the square of the turns ratio N, with the impedance on the primary side $Z_P$ being expressible as a function of the impedance on the secondary side $Z_S$, where $Z_S = j_w C_S$ with $j_w$ being the current in the circuit and $C_S$ being the capacitance on the secondary side, as:

$$Z_P = Z_S/N^2 = 1/(j_w C_S N^2) \qquad \text{[Eq. 11]}$$

In other words, capacitance values are increased by $N^2$ when moving from the secondary to the primary in a boost configuration. Similarly, the above scaling factors of Eqs. 4-10 may be used to scale any desired frequency and nominal load.

Figure 6:
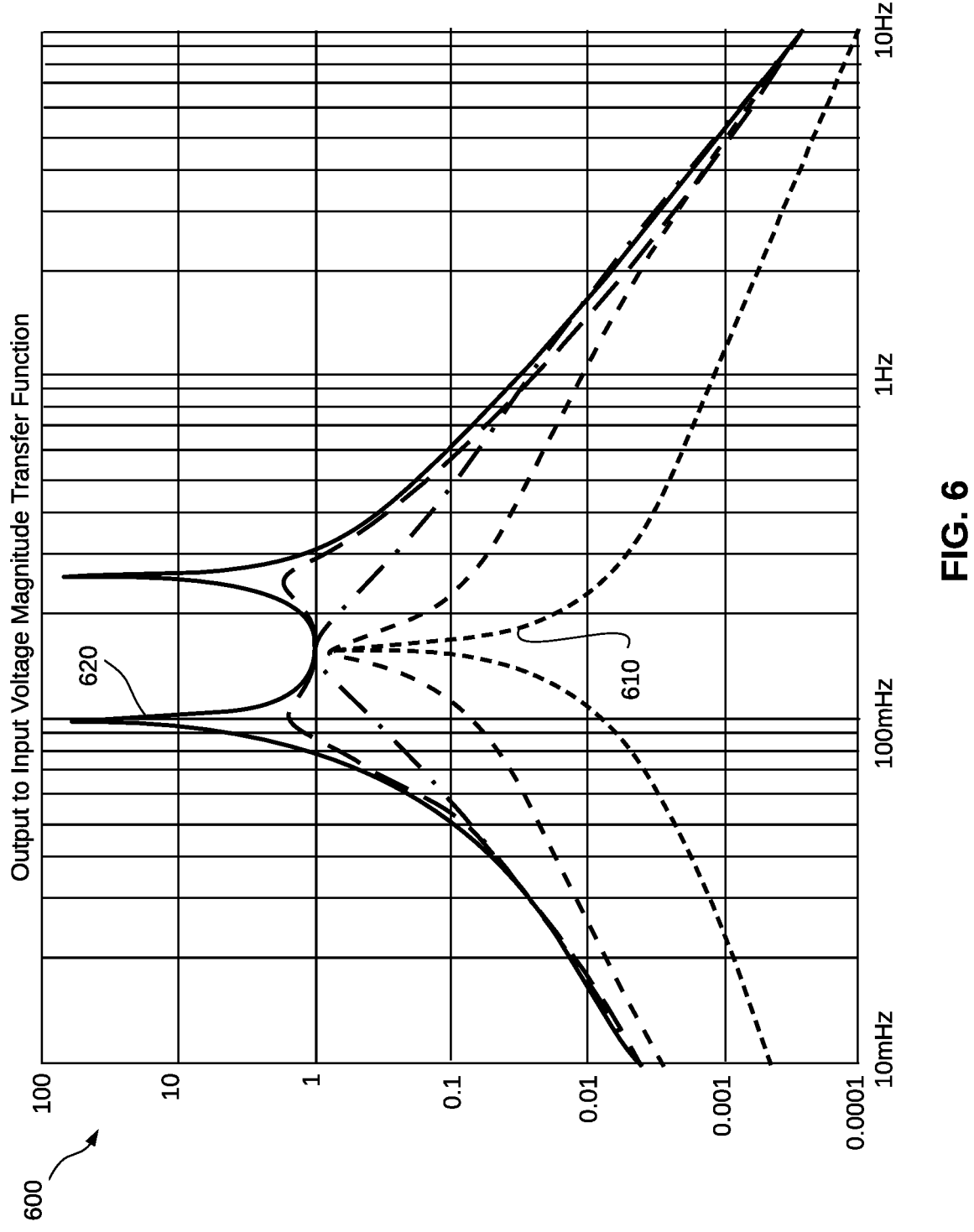
FIG. 6 shows a graph depicting an exemplary output to input voltage magnitude transfer function of a normalized resonant LCLC bandpass network suitable for implementation within an electrosurgical RF generator, in accordance with embodiments.

It is also noted that desirable features of this LCLC network include lossless narrowband filtering of the input signal, as well as maintaining this feature with substantially the same zero insertion loss characteristic over much of the load range at the center frequency. FIG. 6 shows a graph 600 depicting output to input voltage transfer function magnitude ($\|H(f)\|$) of a normalized resonant LCLC bandpass network as a function of frequency, with the different lines corresponding to different load values ranging from short circuit (dashed line 610) to open circuit (solid line 620). The y-axis of graph 600 is dimensionless, while the x-axis is shown herein in units of Hertz. As may be seen in FIG. 6, the zero insertion loss characteristic may be maintained for a frequency range on either side of the center frequency over a range of loads.

One way to achieve the characteristic illustrated in FIG. 6 is to ensure the input impedance presents a power factor of zero to the RF generator with no phase lead or lag at the center frequency. Alternatively, the lossless narrowband filtering over the load range about the center frequency, along with zero-value-switching over the desired range of loads and frequencies, may be achieved by adjusting the series capacitance and shunt inductance resonances by a scale factor and its reciprocal. In this way, ZVS may be maintained both within the passband from the series resonance up to the original center frequency and upward from the second harmonic. An exemplary shift process is shown in FIG. 6, using the following relationships:

$$C1' = K_x/(L1' * \omega_0'^2) \qquad \text{[Eq. 12]}$$

$$L2' = 1/(Kx * C2'^* \omega_0^2)w \qquad \text{[Eq. 13]}$$

Figure 8:
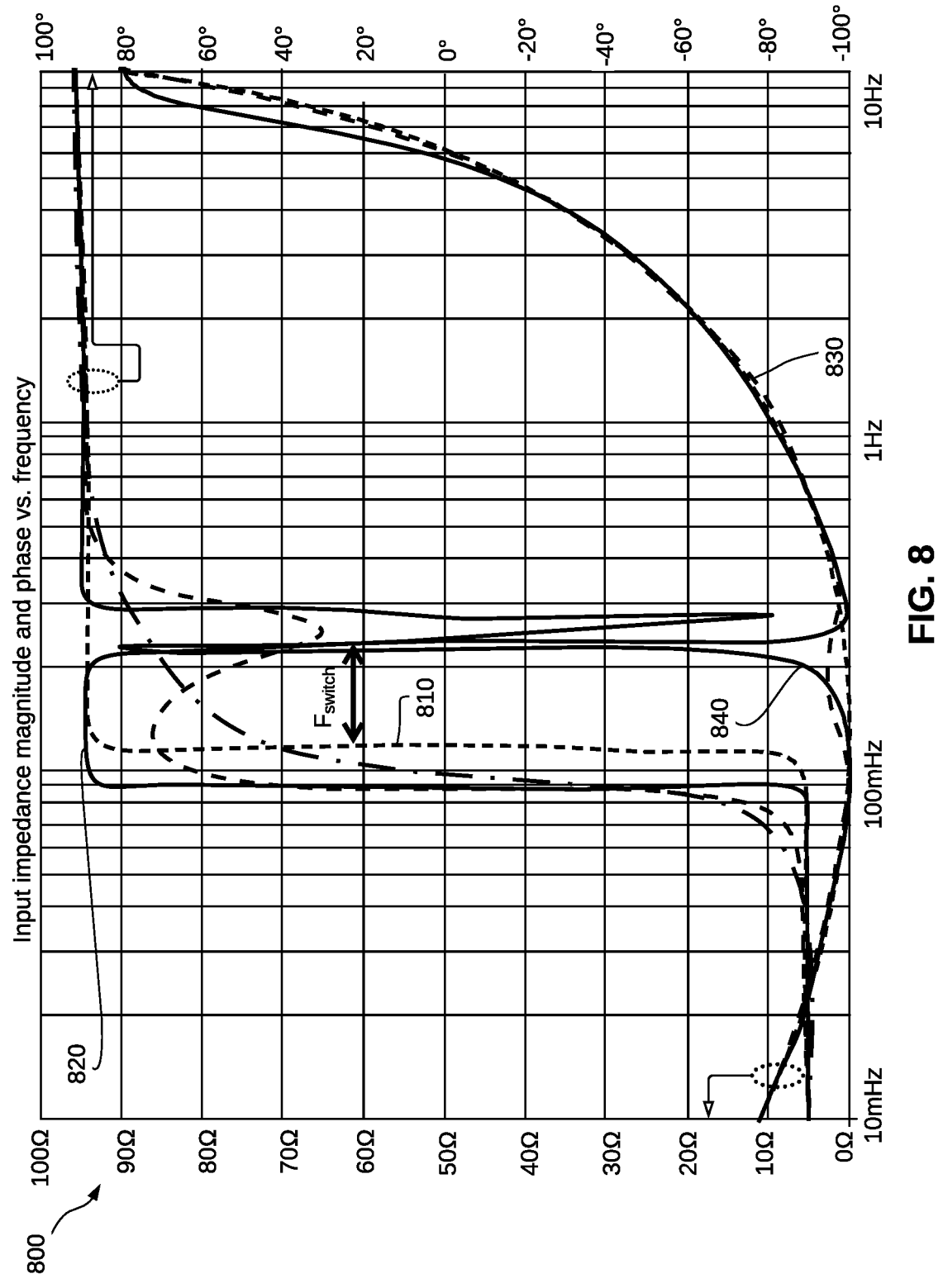
FIG. 8 shows a plot of input impedance magnitude and phase as a function of frequency for a variety of loads, in accordance with embodiments.
Figure 9:
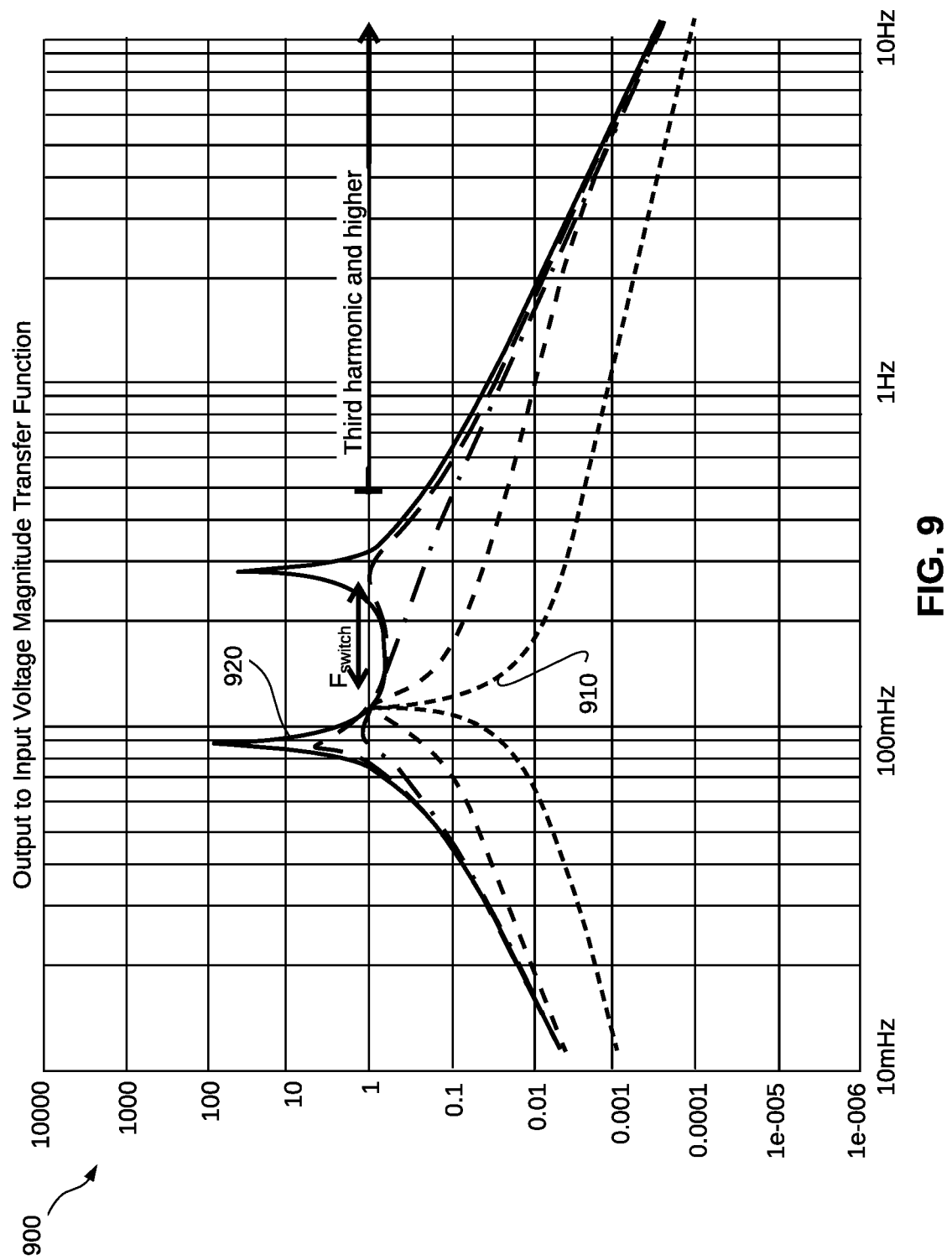
FIG. 9 shows a plot of voltage output to voltage input transfer function magnitude over a range of loads from short circuit to open circuit, in accordance with embodiments.

The resulting plots of input impedance magnitude (left y-axis in units of ohms) and phase (right y-axis in units of degrees) as a function of frequency and the output to input voltage transfer function magnitude ($\|H(f)\|$) of a series frequency-shifted resonant bandpass LCLC network a function of frequency are shown in FIGS. 8 and 9, respectively. In particular, FIG. 8 shows one group of lines representing the phase (right vertical axis) of the series frequency-shifted resonant bandpass LCLC network for various load values ranging from short circuit (dashed line 810) to open circuit (solid line 820), and the magnitude (left vertical axis) of the same series frequency-shifted resonant bandpass LCLC network for various load values ranging from short circuit (dashed line 830) to open circuit (solid line 840). The ZVS range of frequencies is indicated in FIGS. 8 and 9 as Fswitch. In the example shown in FIG. 9, plot 900 illustrates the voltage output to voltage input transfer function magnitude for the range of loads from short circuit to open circuit. The filter is intended to eliminate the third harmonic and higher as indicated in FIG. 9. The shifted, transformed bandpass filter may be further impedance scaled by the output transformer turns ratio to reach the desired values of current and voltage. For instance, the LCLC network may be operated between the series resonant (i.e., $1/\sqrt{L1'^* C1'}$) and parallel resonant frequencies, as shown by the various peaks illustrated in FIG. 6 in certain embodiments. It is further recognized herein that, alternatively, the operation of the LCLC network need not extend to such extremes of frequencies, as potential variations in component tolerances may result in performance outside of the ICE requirements or a calibration or self-test process may be required to obtain such operational limits.

An additional consideration may be that, for operation above the series resonance, such as at what was formerly the center frequency, the LCLC network operation exhibits at least a 3 dB loss at the nominal load (for a Butterworth alignment), as such frequency would correspond to the LP cutoff prior to the transformations. Thus, it may be necessary to adjust the magnitude scaling factor (e.g., output transformer turns ratio, network output impedance) to yield realistic values for the inductance and capacitance.

Figure 11:
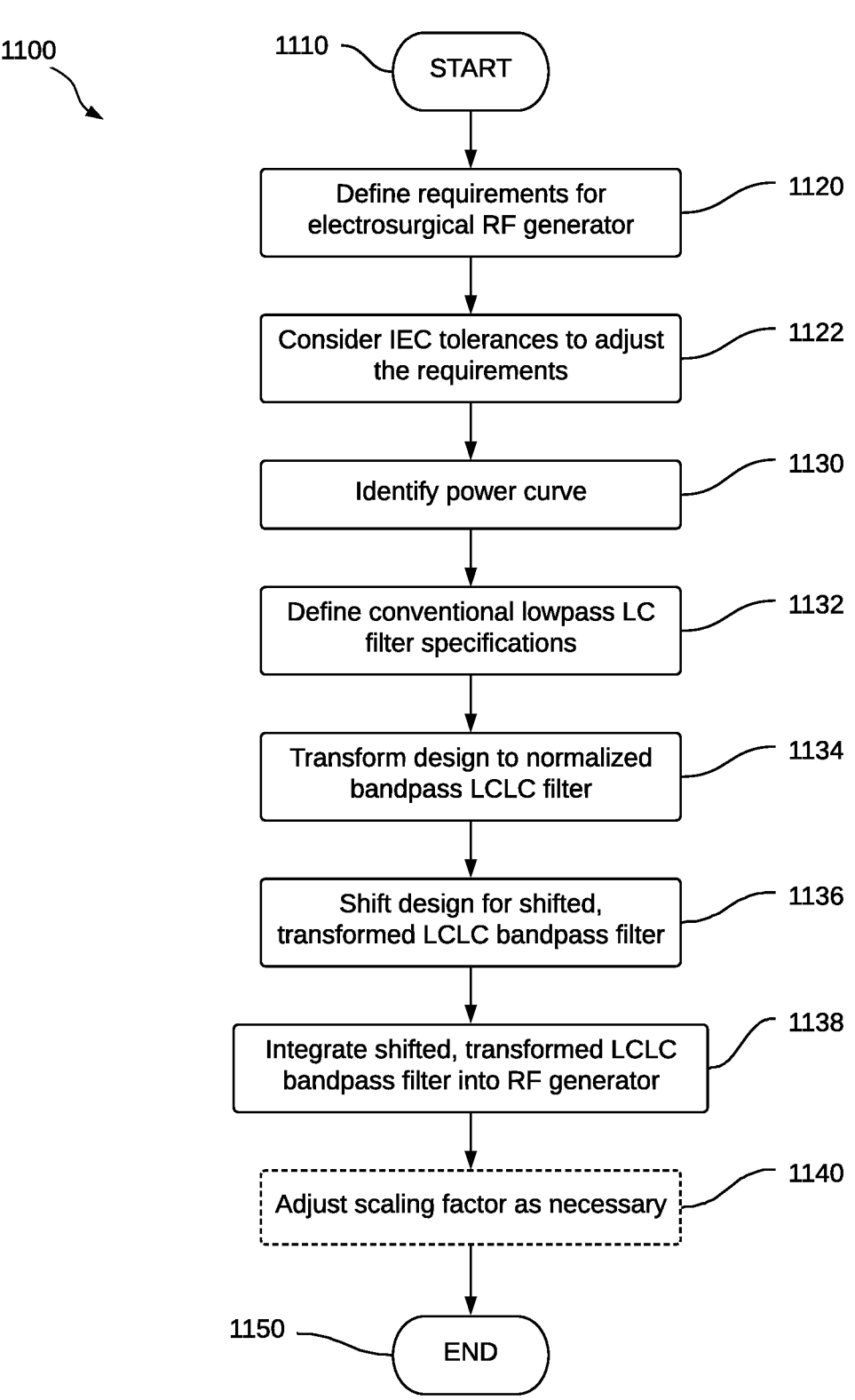
FIG. 11 shows a flow diagram of a method of designing an electrosurgical RF generator, in accordance with embodiments.

An exemplary method of designing an electrosurgical RF generator is illustrated in FIG. 11, in accordance with an embodiment. As shown in FIG. 11, a process 1100 begins with a start step 1110, then proceeds to a step 1120 to define the various requirements for the electrosurgical RF generator. For example, the requirements may include a minimum current and power density to be provided to the electrodes in the electrosurgical device, power levels suitable for particular type and size of specimen of interest, intended wire exposure area, length of wire, wire diameter, impedance of the cable connecting the RF power source to the actuator, impedance load value and range to be provided at the inverter, desired open loop voltage value range, proximity of the wire electrode and the tissue specimen, tissue properties of the specimen of interest, material properties of the electrodes, and desired power settings.

Then, in a step 1122, the IEC requirements for accounting for patient safety may be considered. For example, the tolerance in variations in power outputs may be taken into consideration in specifying the power ranges to be output from the electrosurgical RF generator system such that, even under near short circuit conditions, the electrosurgical system may function without harming the patient. Other considerations may include tolerances in power limiting, harmonic content, and/or accounting for other variations in performance that may occur during normal or extraordinary operational conditions of the electrosurgical system.

In a step 1130, one or more power curve envelopes may be identified. In an example, known output characteristics of resonant inverters (e.g., as shown in FIG. 2 described above) may provide a foundational starting point. In a step 1132, the power curve and the defined parameters from steps 1120 and 1122 are used to define conventional lowpass LC filter specifications (e.g., as shown in the top half of FIG. 5). It is recognized herein that, in certain cases, the conventional lowpass LC filter may be sufficient for a specific electrosurgical application. In other cases, the conventional lowpass LC filter specifications may be transformed to define a normalized bandpass LCLC filter, in a step 1134 (e.g., as shown in the bottom half of FIG. 5). Then, the design from step 1134 may be shifted to derive a shifted, transformed LCLC bandpass filter design in a step 1136 (e.g., as shown in FIG. 7). The resulting LCLC bandpass filter design may be incorporated into an overall electronics design of the electrosurgical RF generator in a step 1138. In an optional step 1140, the scaling factor of the transforming and/or shifting of steps 1134 and 1136 may be adjusted, if so required in the integration of the LCLC bandpass filter design into the electrosurgical RF generator. Process 1100 is terminated in an end step 1150.

In accordance with embodiments, a design operation for the electrosurgical RF generator, such as the example illustrated in FIG. 11, may include some or all of the following:

1) An operation may include identifying power curve envelope candidate(s).

2) An operation may include recording an initial real power versus tissue resistance envelope.

3) An operation may include specifying the power curve.

4) An operation may include using the ideal open loop output characteristics of a generator, or inverter, to determine the characteristic output impedance of the electrosurgical RF generator. Wherein, for example, the characteristic output impedance can be 130 ohms and have a 406 W peak.

5) An operation may include identifying a current and voltage limiting region. In such regions near the voltage and current limit intersections when the power is decreasing, a 20% tolerance in power accuracy, typically required by the International Electrotechnical Commission (IEC), may be interpreted as having a corresponding tolerance in the resistance intersect points as well. The tolerance in both resistance and power is often unappreciated by those who are specifying electrosurgical systems.

6) An operation may include consideration of the region of uncertainty in power on the power curve to determine a tolerance in the voltage and current limits. This is juxtaposed to any implied tolerance of zero, that some would find if assuming zero tolerance of the resistance axis in this plot, near short or open circuit (because the power approaches zero), or at resistance intersect points on the power curve, where the power drops from its maximum limit.

7) An operation may be avoiding energy overdosage and maintain monotonic power settings (steps that increase or decrease without going unexpectedly in the opposite direction of what the operator intended). For example, at a plus 20% power maximum the intersect in current may occur at minus 20% in resistance, or 50 ohms, and therefore result in a maximum current of 3 Arms. This may imply that a +/−20% tolerance of the 2.5 Arms is nominal. And the same may be said for the voltage.

8) An operation may include modifying the power curve specification to instead limit the power. For example, the power may be less than 400 W maximum, which includes a 20% tolerance margin, which may instead limit the nominal power to 333 W, instead of 375 W, but otherwise retain the same voltage and current limits. This modification may not affect the necessary open loop characteristic but may rather affect only the range over which the power must be limited by the control loop. This may ensure that the IEC maximum limit of 400 W not be exceeded for electrosurgical systems.

9) An operation may include calculating a first iteration of an output network characteristic impedance that may be used for initial tissue testing.

10) An operation may include using a pulse width modulation through an LCLC resonant network.

11) An operation may include adjusting the input voltage via a secondary DC-DC buck or boost stage following a first stage power factor correction (PFC) AC-DC conversion.

12) An operation may include designing to the power curve by switching frequency modulation of the LCLC resonant network entirely and using a fixed medical power supply; the fixed medical power supply may be 48 VDC. Frequency modulation schemes have been successfully employed in LLC resonant converters and may be used in everything from lighting to battery charging applications. One advantage of using a frequency modulation scheme with a fixed medical power supply of 48 VDC are the abundance of power supplies and, the potential application of multiple power sources. Further benefits are that the system development can proceed more rapidly in that a second stage may not have to be simultaneously designed and multiple control loops, with the potential for complex interactions, may not necessarily be developed.

13) An operation may include determining a harmonic content of the output waveform. It is recognized herein that most LLC resonant designs are converters and not inverters, meaning that the switching waveforms may be rectified, and subsequently low pass filtered at the output to yield the necessary DC voltage. At short circuit they have good attenuation of the high frequency content in series form, but in parallel forms there is not much in the way of current limiting or DC protection of the transformer under fault. And at light loads to open circuit, series LLC networks have nearly square wave output waveforms before they are rectified, and low pass filtered. Such high, primarily odd-order, harmonic content, as shown and described in the figures, in inverter applications like electrosurgery may lead to issues with high peak voltages at light loads along with high frequency leakage. These issues become undesirable features due to capacitive coupling to alternate paths that can lead to RF burns of a patient or others in the surgical field who are in contact with the patient or operating the system. Therefore, it may be preferrable to reduce, or eliminate, the high-frequency content of the RF waveform in electrosurgical applications, generally. While strong odd harmonic content is an ever-present problem at open circuit for series LLC and may still be designed to such a point that it is tolerable in some electrosurgical applications, it should be noted that strong even-order harmonic content may also be present due to the dead-time (or PWM at low power levels) during nominal loading situations. Here, tolerable may be defined such that for a given LLC output one may modify to an LCLC topology that is mostly LLC in nature but includes a modest low pass filter feature at or near the 5th harmonic and above for a 200 kHz minimum frequency system, that is typically required by the IEC. However, these modifications may affect the zero-voltage-switching behavior. Additionally, the current system may have increased coupling capacitance compared to typical electrosurgical applications. Further, series LLC and PWM control of the power may be excluded from application with the methods described here as they may conflict with minimizing the frequency content. Contrastingly, an LCLC network may be used to achieve a bandpass limiting function over the load impedance range. 14) An operation may include utilizing a bandpass network that simultaneously maintains ZVS over the entire load range of short circuit to open circuit, meets a selected, near-ideal, characteristic output impedance over that load range, and limits the harmonic frequency content over the entire load range to levels that would be safely within IEC limits. Typical design procedures for LCLC bandpass filters (BPF) in design of RF networks may yield networks intended for near lossless narrowband filtering with a power factor of zero, when driven at the center resonant frequency. A power factor of zero may be undesirable, as it may not meet ZVS criteria, when it comes to maintaining ZVS over the load impedance range.

15) An operation may include further transforming the normalized filter to the desired center frequency, $f_c$, and load impedance, Ru, via scaling factors, $K_f$ and $K_m$, respectively, of the filter components given by Eqs. 4-10 above.

Figure 10:
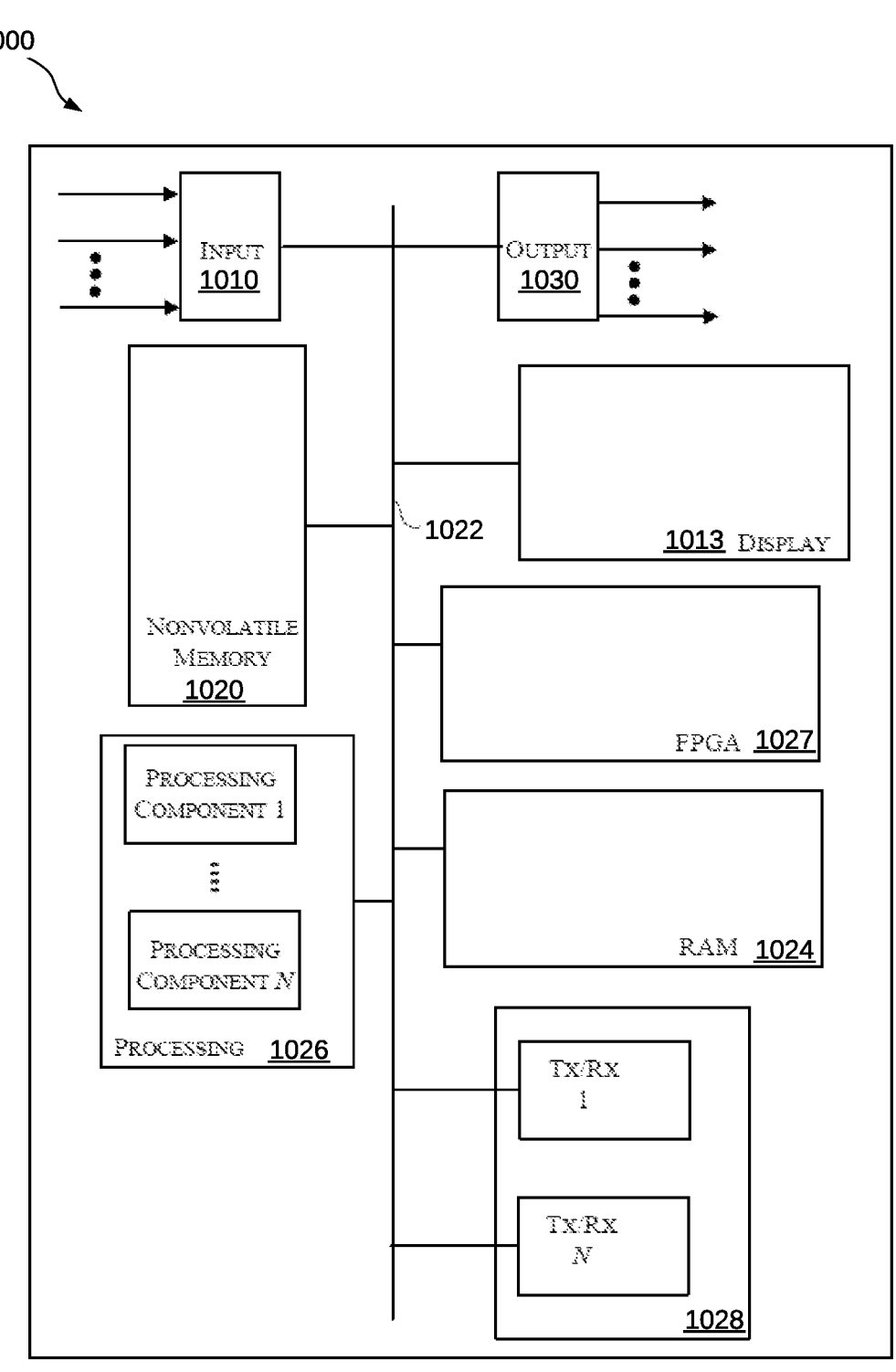
FIG. 10 shows a block diagram depicting physical components that may be utilized to realize one or more aspects of the electrosurgical RF generator design, in accordance with embodiments.

Referring to FIG. 10 for example, shown is a block diagram depicting physical components that may be utilized to realize one or more aspects of the electrosurgical RF generator. As shown, in this embodiment a display 1012 and nonvolatile memory 1020 are coupled to a bus 1022 that is also coupled to random access memory ("RAM") 1024, a processing portion (which includes N processing components) 1026, a field programmable gate array (FPGA) 1027, and a transceiver component 1028 that includes N transceivers. Although the components depicted in FIG. 10 represent physical components, FIG. 10 is not intended to be a detailed hardware diagram; thus, many of the components depicted in FIG. 10 may be realized by common constructs or distributed among additional physical components. Moreover, it is contemplated that other existing and yet-to-be developed physical components and architectures may be utilized to implement the functional components described with reference to FIG. 10.

Display 1012 generally operates to provide a user interface for a user, and in several implementations, the display is realized by a touchscreen display. For example, nonvolatile memory 1020 is non-transitory memory that functions to store (e.g., persistently store) data and machine readable (e.g., processor executable) code (including executable code that is associated with effectuating the methods described herein). In some embodiments, for example, nonvolatile memory 1020 includes bootloader code, operating system code, file system code, and non-transitory processor-executable code to facilitate the execution of the method described with reference to FIG. 10. Nonvolatile memory 1020 may also be used to realize the reliability data datastore and may be used to store the recorded telemetry data (e.g., tuning events such as, e.g., lead screw turns and trajectories of capacitor positions).

In many implementations, nonvolatile memory 1020 is realized by flash memory (e.g., NAND or ONENAND memory), and it is contemplated that other memory types may be utilized. Although it may be possible to execute the code from nonvolatile memory 1020, the executable code in the nonvolatile memory is typically loaded into RAM 1024 and executed by one or more of the N processing components in processing portion 1026.

In operation, the N processing components in connection with RAM 1024 may generally operate to execute the instructions stored in nonvolatile memory 1020. For example, non-transitory processor-executable instructions to effectuate the methods described herein may be persistently stored in nonvolatile memory 1020 and executed by the N processing components in connection with RAM 1024. For example, processing portion 1026 may include a video processor, digital signal processor (DSP), graphics processing unit (GPU), and other processing components.

In addition, or in the alternative, field programmable gate array (FPGA) 1027 may be configured to effectuate one or more aspects of the methodologies described herein (e.g., the methods described with reference to FIG. 11). For example, non-transitory FPGA-configuration-instructions may be persistently stored in nonvolatile memory 1020 and accessed by FPGA 1027 (e.g., during boot up) to configure FPGA 1027 to effectuate the functions of the electrosurgical RF generator described herein.

The depicted transceiver component 1028 may include N transceiver chains, which may be used for communicating with external devices via wireless or wireline networks. Each of the N transceiver chains may represent a transceiver associated with a particular communication scheme (e.g., WiFi, Ethernet, Profibus, etc.).

In some implementations, the design method described herein may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of the method in response to instructions stored electronically on an electronic storage medium. The one or more processing devices may include one or more devices configured through hardware, firmware, and/or software to be specifically designed for execution of one or more of the operations of the method.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. A radiofrequency (RF) generator for use with an electrosurgical system, the RF generator comprising:
   a shifted, transformed LCLC bandpass filter, wherein the shifted, transformed LCLC bandpass filter is configured for allowing the RF generator to operate using a single electrosurgical power setting while preventing overheating of the electrosurgical system.

2. The RF generator of claim 1, wherein the LCLC bandpass filter is configured to operate with a specified power curve such that an operating current generated by the RF generator is folded back when approaching short circuit conditions.

3. The RF generator of claim 2, further comprising a fixed, medical power supply, wherein the specified power curve is modified by switching frequency modulation of the LCLC bandpass filter.

4. The RF generator of claim 1, wherein the LCLC bandpass filter is configured for ensuring the RF generator remains within International Electrotechnical Commission (IEC) limits for medical devices over a range of load levels.

5. The RF generator of claim 1, wherein the shifted, transformed LCLC bandpass filter is further configured to provide a lossless narrowband filtering of an input signal over a load range about a center frequency.

6. The RF generator of claim 1, wherein the shifted, transformed LCLC bandpass filter is further configured to exhibit an input impedance with a power factor of zero to the RF generator with substantially no phase lead and phase lag at a center frequency.

7. The RF generator of claim 1, wherein the LCLC bandpass filter is further configured for implementing a pulse width modulation (PWM) scheme.

8. The RF generator of claim 6, further comprising:

a first stage power factor correction (PFC) alternating current (AC)—direct current (DC) conversion;

at least one of a secondary DC-DC buck stage and a secondary DC-DC boost stage configured for adjusting an input voltage to the LCLC bandpass filter.

9. The RF generator of claim 1, wherein the LCLC bandpass filter is configured for maintaining zero-voltage switching (ZVS) over a load range substantially from short circuit to open circuit, meeting a selected, near-ideal, characteristic output impedance over the load range, and limiting a harmonic frequency content of RF generated over the load range to levels within International Electrotechnical Commission (IEC) limits.

* * * * *